US006940982B1

(12) United States Patent
Watkins

(10) Patent No.: US 6,940,982 B1
(45) Date of Patent: Sep. 6, 2005

(54) ADAPTIVE NOISE CANCELLATION (ANC) FOR DVD SYSTEMS

(75) Inventor: Daniel Watkins, Saratoga, CA (US)

(73) Assignee: LSI Logic Corporation, Milpitas, CA (US)

( * ) Notice: Subject to any disclaimer, the term of this patent is extended or adjusted under 35 U.S.C. 154(b) by 789 days.

(21) Appl. No.: 09/821,555

(22) Filed: Mar. 28, 2001

(51) Int. Cl.[7] .......................... H04B 1/00; H04B 15/00; H03B 29/00; A61F 11/06

(52) U.S. Cl. ..................... 381/71.1; 381/119; 381/94.3

(58) Field of Search ............................. 381/71.1, 71.2, 381/71.3, 71.11, 94.1, 94.2, 94.3, 119, 122, 381/63, 123, 83, 107

(56) References Cited

U.S. PATENT DOCUMENTS 5,444,785 A * 8/1995 Izawa et al. .................. 381/63
5,541,999 A * 7/1996 Hirai .......................... 381/107
5,668,339 A * 9/1997 Shin ........................... 381/123
5,729,614 A * 3/1998 Nagata et al. ................ 381/83
6,068,489 A * 5/2000 Nagata et al. ................ 381/63
6,139,329 A * 10/2000 Mino et al. ............. 434/307 A
6,246,773 B1 * 6/2001 Eastty ...................... 381/71.11
6,442,280 B1 * 8/2002 Ito ............................. 381/83
6,740,803 B2 * 5/2004 Brinkman et al. ............ 84/609

* cited by examiner

*Primary Examiner*—Stella Woo
(74) *Attorney, Agent, or Firm*—Christopher P. Maiorana, P.C.

(57) ABSTRACT

An apparatus comprising an input, a noise cancellation circuit, an audio circuit and a mixing circuit. The input may be configured to receive one or more input signals. The noise cancellation circuit may be configured to generate a first processed audio signal having reduced noise in response to the input signals. The audio circuit may be configured to generate a second audio signal from a digital source. The mixing circuit may mix the processed audio signal and the second audio signals to generate an output signal.

20 Claims, 3 Drawing Sheets

ADAPTIVE NOISE CANCELLATION (ANC) FOR DVD SYSTEMS

FIELD OF THE INVENTION

The present invention relates to a method and/or architecture for adaptive noise cancellation (ANC) generally and, more particularly, to an adaptive noise cancellation system that may be used with digital versatile disk (DVD) systems.

BACKGROUND OF THE INVENTION

Conventional DVD players do not support adaptive noise cancellation technology. Noise cancellation can be incorporated into microphones, but at a cost that may be prohibitive for consumer products, such as karaoke players. Players used for karaoke have noise that is inputted to the microphone and propagated to the speakers. Furthermore, there is no anti-noise support for the speakers.

SUMMARY OF THE INVENTION

The present invention concerns an apparatus comprising an input, a noise cancellation circuit, an audio circuit and a mixing circuit. The input may be configured to receive one or more input signals. The noise cancellation circuit may be configured to generate a first processed audio signal having reduced noise in response to the input signals. The audio circuit may be configured to generate a second audio signal from a digital source. The mixing circuit may mix the processed audio signal and the second audio signals to generate an output signal.

The objects, features and advantages of the present invention include providing a method and/or architecture for ANC in digital versatile disk (DVD) systems that may provide (i) a variety of features such as noise detect, noise suppress and anti-noise that may each be optionally enabled at different programmable dB levels; (ii) dynamic anti-noise processing such that delay from sound input to sound processed for anti-noise output is synchronized even with lengthy intermediate audio processing involved such as 3D Audio or Karaoke; (iii) enhanced ANC functions such as programmable detect, suppress and anti-noise and/or (iv) a single DVD system to handle all room, DVD playback, browser playback, and browser capture processing.

BRIEF DESCRIPTION OF THE DRAWINGS

These and other objects, features and advantages of the present invention will be apparent from the following detailed description and the appended claims and drawings in which:

DETAILED DESCRIPTION OF THE PREFERRED EMBODIMENTS

Figure 1:
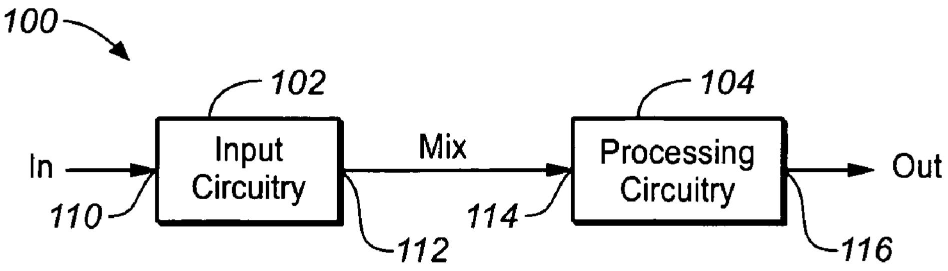
FIG. 1 is a block diagram of a preferred embodiment of the present invention.

Referring to FIG. 1, a block diagram of a circuit 100 is shown in accordance with a preferred embodiment of the present invention. The circuit 100 generally comprises a block (or circuit) 102 and a block (or circuit) 104. The circuit 102 may be implemented as an input circuit. The circuit 104 may be implemented as a processing circuit. The input circuit 102 may have an input 110 that may receive an input signal (e.g., IN) and an output 112 that may present a signal (e.g., MIX). The signal MIX may be presented to an input 114 of the processing circuit 104. The processing circuit 104 may have an output 116 that may present an output signal (e.g., OUT).

The circuit 100 may be implemented as an adaptive noise cancellation (ANC) system. For example, the circuit 100 may be implemented within consumer DVD players. The circuit 100 may enable stationary noise detect, then implement optional noise suppress, karaoke processing, anti-noise, or other appropriate type audio processing. The circuit 100 may also provide sound detect and reporting features for DVD players, dynamic anti-noise processing for introduced delay and band programmable based stationary noise detect, suppress and anti-noise. The system 100 may also provide remote noise detect, suppress and anti-noise processing. Additionally, the circuit 100 may be implemented as an ANC system for browser functions.

Figure 2:
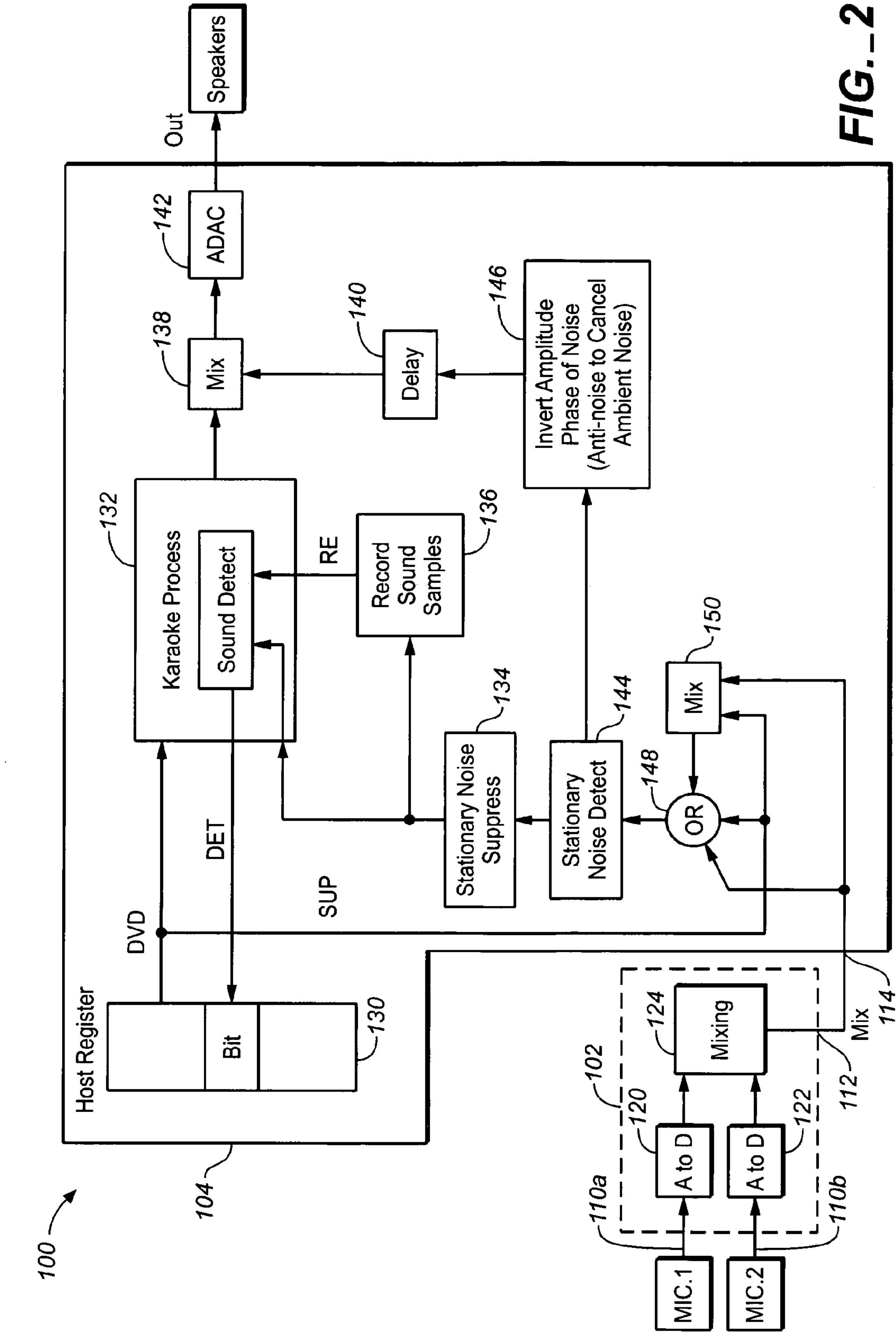
FIG. 2 is a detailed block diagram of the circuit of FIG. 1.

Referring to FIG. 2, a detailed block diagram of the circuit 100 is shown. The circuit 102 may comprise a circuit 120, a circuit 122 and a circuit 124. The circuits 120 and 122 may be implemented as analog-to-digital converter circuits. The circuit 124 may be a mixing circuit. A first microphone (e.g., MIC_1) may present a signal to a first input 110*a*. A second microphone (e.g., MIC_2) may present a signal to a second input 110*b*. The mixing circuit 124 may combine the digital signals received from the circuits 120 and 122 to present the signal MIX.

The circuit 104 generally comprises a circuit 130, a circuit 132, a circuit 134, a circuit 136, a circuit 138, a circuit 140, a circuit 142, a circuit 144, a circuit 146, a circuit 148, and a circuit 150. The circuit 130 may be implemented as a register. The circuit 132 may be implemented as a karaoke processor or other sound detect processor. The circuit 134 may be a stationary noise suppress circuit. The circuit 136 may be a record sound sample circuit. The circuit 138 may be a mixing circuit. The circuit 140 may be a delay circuit. The circuit 142 may be an analog-to-digital audio converter circuit. The circuit 144 may be a stationary noise detect circuit. The circuit 146 may be used to invert the amplitude phase of the noise. The circuit 148 may be a multiplexor or other appropriate logic. The circuit 150 may be a mixing circuit.

The circuit 100 may provide an ANC system for DVD players. While two microphone inputs 110*a*–110*b* are shown, one or more microphone inputs may be implemented. Each microphone input 110*a*–10*b* may have a corresponding analog-to-digital convert 120, 122, etc. The outputs of the ADCs 120 and 122 may be mixed (by the mixing circuit 124) to provide a single feed (the signal MIX) to the processing circuit 104. The digital feed MIX may be presented to a DVD silicon IC (e.g., the processing circuit 104). The processing circuit 104 may optionally include a CPU or an A/V decoder (both of which are not shown) which may control the various circuits 130–150. Additionally, the processing circuit 104 may implement an embedded postal DSP circuit (not shown) to allow the ANC and sound sample process in DSP code. The circuit 100 may also implement software that may eliminate background noise from speech and other signals. For example, the ANC firmware may implement Clearspeech® by Network Connections Technologies, Inc.

The circuit 100 of FIG. 2 is segmented into the stationary noise detect circuit 144, the stationary noise suppress circuit 134 and the anti-noise circuit 146. Such a case may allow a user to (i) program stationary bands of noise to detect and/or suppress, (ii) have anti-noise on independently and/or (iii) allow mixing of other audio such as DVD playback, prior to the anti-noise. Once anti-noise is outputted, the microphone inputs MIC_1 and MIC_2 may provide reference to pick up the difference between ambient noise and anti-noise. The difference may be implemented to adjust the anti-noise over time as needed.

Local memory and firmware may record sound samples and perform sound detect and reporting. Typical sounds to detect are phone ring, door bell, leaf blower, dog bark, lawn mower, frogs, crickets, radio in the room, speaker phone in the room, etc. To reduce such sounds in recording, the user may provide a sample sound to the system. When enabled, the system 100 may search for the background sounds and report detection.

Additionally, other local memory and firmware may detect frequency overlapping of HomeRF and IEEE 802.11 and provide anti-band strength of the one the user chooses. The system 100 enables browser audio, such as VoIP or Internet radio to have ANC, with Karaoke and sound detect options as well.

Figure 3:
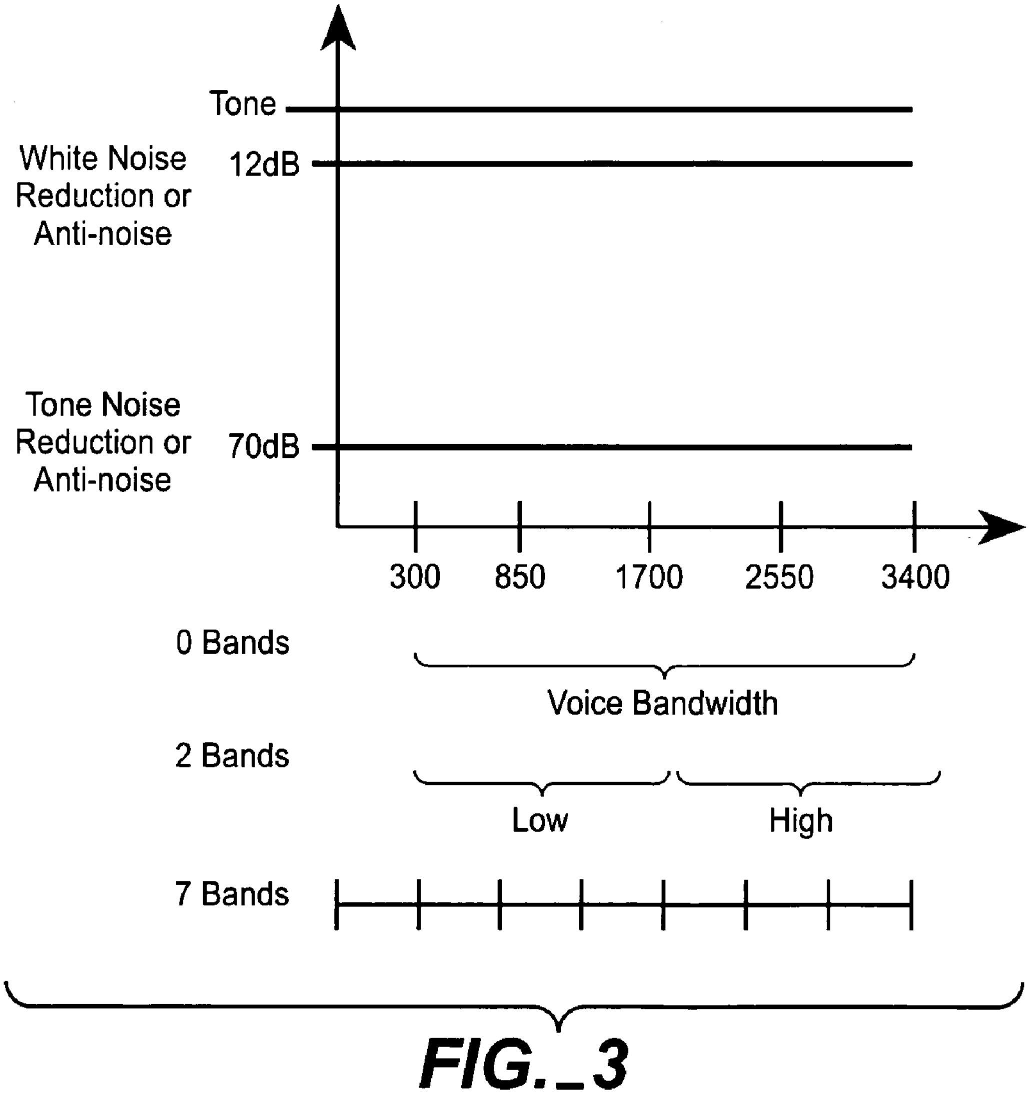
FIG. 3 is a graph illustrating an operation of the present invention.

Referring to FIG. 3, an example implementation of audio bands is shown. The voice bandwidth can be divided into bands each for detection, suppression, and anti-noise in a programmable way. The more bands available to program, the more millions of instructions per second (mips) are consumed. For example, processing 7 bands instead of 2 bands as shown, generally requires more mips.

Figure 4:
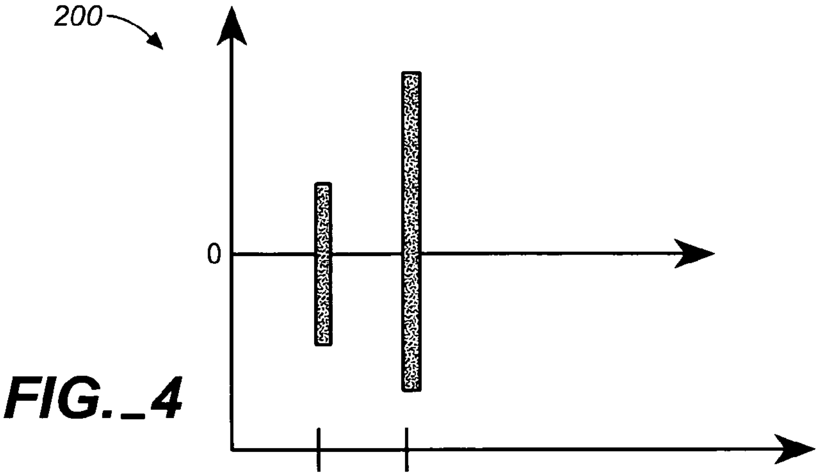
FIG. 4 is a graph illustrating an example operation of the present invention.
Figure 5:
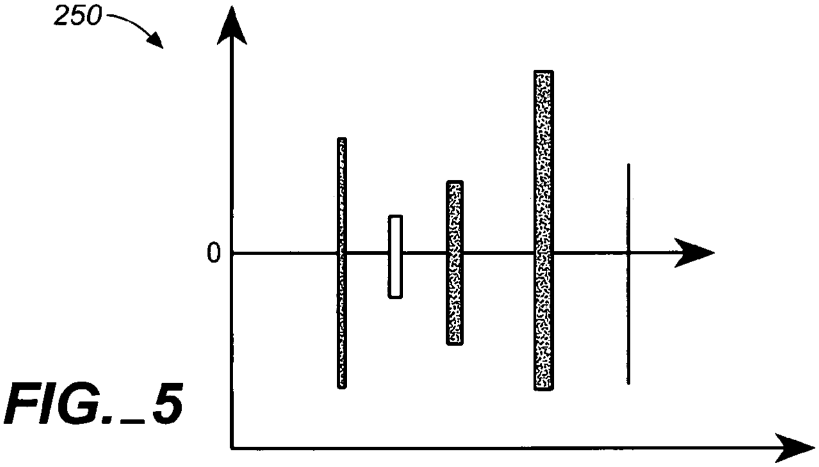
FIG. 5 is a graph illustrating the reception of the example sound of FIG. 4.

Referring to FIG. 4, an example sound sample 200 is shown. In one example, the sound sample 200 may be a two tone door bell sound sample. Referring to FIG. 5, an example reception 250 of the sound sample 200 is shown.

Figure 6:
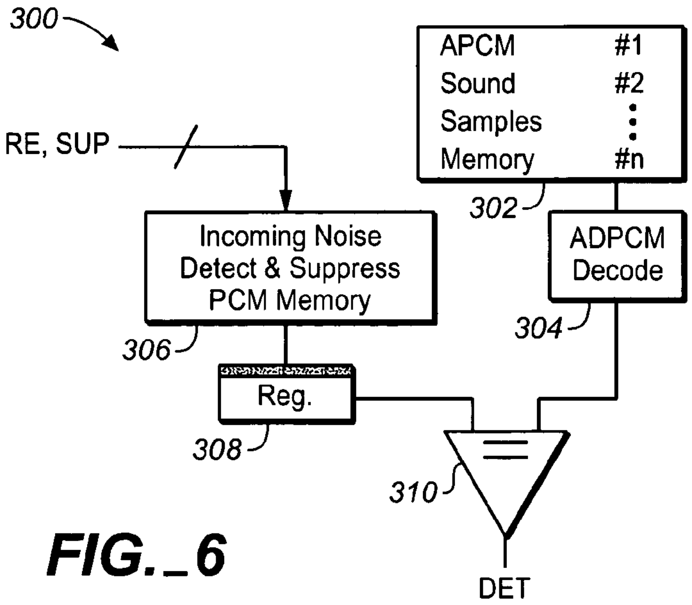
FIG. 6 is a detailed block diagram of a detect circuit implemented in connection with the present invention.

Referring to FIG. 6, an example sound detect circuit 300 is shown. The sound detect circuit 300 may be implemented within the Karaoke process block 132 of FIG. 2. The sound detect circuit 300 generally comprises an audio pulse code modulation (APCM) memory 302, an adaptive differential pulse code modulation (ADPCM) decode circuit 304, an incoming noise detect and suppress PCM memory 306, a register 308 and a comparator 310. ADPCM is Adaptive Differential Pulse Code Modulation. ADPCM is similar to PCM audio encoding where the encoding is the difference between the audio sample amplitude and the predicted amplitude. The APCM memory 302 may store sound samples to be used to match incoming noise. If a match occurs (less than 10% difference, for example) a match may occur and the noise may be filtered. The matching process may be repeated as required for a number n sound samples, where n is an integer. Additionally, if the incoming noise is not already sampled, the noise may be recorded to a sound sample.

The APCM memory circuit 302 may present a signal to the ADPCM decode circuit 304. The ADPCM decode circuit 304 may then present a signal to the comparator 310. The incoming detect and suppress circuit 306 may receive the signal RE and the signal SUP. The circuit 306 may then present a signal to the register 308. The register 308 may then present a signal to the comparator 310. When a match occurs within the comparator 310, the sound detect circuit 300 may notify the circuit 100 of a sound sample to be filtered.

Alternatively, user sound samples may be inputted and audio may be cleansed and stored on a DVD system. The stored sounds may then be used to identify incoming audio and process the audio according to pre-determined programmable parameters. The circuit 100 may provide adaptive noise cancellation (ANC) technology in DVD players.

For the Karaoke market, microphone input processing features of ANC enable clear recording and speaker output with anti-noise to eliminate room noise for listeners. However, many additional markets may benefit from noise detection, suppression and anti-noise to eliminate room noise for the listener. The circuit 100 may notify the user of noise through an audio and/or video interface. Furthermore, the user may be selectively notified of recorded sounds.

The circuit 100 may support ANC functions on a DVD system, such as noise detect, noise suppress and anti-noise. Each optionally enabled and at different programmable dB levels. The circuit 100 may allow ANC functions to be supported on a DVD system with karaoke, where typical karaoke functions such as key control, voice cancellation, and surround are supported with measured amounts of stationary noise mixed from the microphone inputs. Optionally, the circuitry 100 may implement microphone input noise detect and suppress. The circuit 100 may allow ANC functions to be supported on a DVD system where the DVD bitstream feed may have ANC operations done, such as noise detect, noise suppress and anti-noise, each optionally enabled and at different programmable decibel levels. The circuit 100 may allow ANC functions to be supported on DVD systems that perform stationary noise detect and suppress, enabling cleanly recorded sound samples to be used for sound detect.

The circuit 100 may allow dynamic anti-noise processing such that delay from sound input to sound processed for anti-noise output is synchronized even with lengthy intermediate audio processing involved such as 3D Audio or Karaoke. However, synchronization may have an increased new fixed latency based on the newly introduced delay via the circuit 100. The circuit 100 may allow enhanced ANC functions to be supported on a DVD system, such as programmable type of detect, suppress and anti-noise. Programmability may be on an audio band basis, such as shown in FIGS. 3, 4 and 5, or on ANC features of each function basis, such as detect and suppress frequencies lower than 1 KHz audio (e.g., a leafblower, dog bark, lawn mower, frog sounds, radio in room, speaker phone, etc.) for someone listening to headphones for a karaoke playback and microphone feed. Thus, all stationary noise suppression, such as the leafblower, dog bark, lawn mower, frog sounds, radio in room, speaker phone, etc., may be accomplished.

The circuit 100 may allow mixing of audio that has had noise detect and suppress with other audio, such as from a DVD playback, then having anti-noise mixed. The circuit 100 may enable a single DVD system to handle all room, DVD playback, browser playback, and browser capture processing. The circuit 100 may allow ANC and sound detect and noise suppress functions to be supported on a DVD system for browser VoIP, Internet audio and other browser based audio. For example, real audio playback of a radio station may have noise that can be detected and suppressed for better listening. The circuit 100 may allow a user to record sound samples and input audio and monitored for the sounds. When the sound are detected, the user may be notified via audio or video. The circuit 100 may allow programmable types of sound detect notification, such as change in audio output (e.g., mute all sound except for detected sound, or optionally amplify sound) or change in video output (e.g., blinking object on the display, text on the display with option to name the detected sound), change in A/V programming or change in audio and video output.

The circuit 100 may allow user notification of a VoIP call from browser and the ANC may be engaged automatically. The circuit 100 may allow remote noise detect, suppress and anti-noise as well as sound detect to be enabled. For example, the browser may have a server role, where a remote web access may implement an ANC and sound detect technology enabled DVD player to assess the sounds of the rooms, even record the sounds (or just log with time and sound detected) for review at a later time. The circuit 100 may allow a DVD player with ANC architecture to (i) allow a microphone input to be multiplexed with a DVD bitstream input to feed a stationary noise detect function, (ii) provide a stationary noise suppress function, and (iii) provide a sound detect function. The feed audio and recorded sound samples may then be compared and an anti-noise function and mixed on the output such that A/V synchronization is maintained.

While the invention has been particularly shown and described with reference to the preferred embodiments thereof, it will be understood by those skilled in the art that various changes in form and details may be made without departing from the spirit and scope of the invention.

What is claimed is:

1. An apparatus comprising:

an input circuit configured to receive one or more input signals;

a noise cancellation circuit configured to (i) generate a first processed audio signal having reduced noise in response to said input signals, (ii) perform noise detection at a first programmable decibel level and (iii) perform noise suppression at a second programmable decibel level;

an audio circuit configured to generate a second audio signal from a digital source; and a mixing circuit configured to mix said processed audio signal and said second audio signals to generate an output signal.

2. The apparatus according to claim 1, wherein said apparatus comprises a digital versatile disk (DVD) system.

3. The apparatus according to claim 1, wherein said noise cancellation circuit is further configured to perform one or more types of noise cancellation.

4. The apparatus according to claim 3, wherein said types of noise cancellation are selected from the group consisting of (i) noise detect, (ii) noise suppress, (iii) anti-noise and (iv) other appropriate types of noise cancellation.

5. The apparatus according to claim 3, wherein each of said one or more types of noise cancellation are optionally enabled.

6. The apparatus according to claim 5, wherein each of said one or more types of noise cancellation operate at different dB levels.

7. The apparatus according to claim 5, wherein each of said one or more types of noise cancellation are programmable.

8. The apparatus according to claim 1, wherein said apparatus is configured to support a DVD system and perform key control, voice cancellation, and surround with a measured amount of stationary noise mixed from the one or more inputs signals.

9. The apparatus according to claim 1, wherein said apparatus is configured to support a DVD bitstream feed and further perform and anti-noise processing.

10. The apparatus according to claim 1, wherein said apparatus is configured to support a DVD system and provide stationary noise detect and suppress to enable recorded sound samples to be used for sound detect.

11. The apparatus according to claim 1, wherein said noise cancellation circuit is further configured to provide dynamic anti-noise processing to allow a delay from said input to be processed with said noise cancellation and be synchronized with said second audio signal.

12. The apparatus according to claim 11, wherein said dynamic anti-noise processing compensates for a fixed latency based on an introduced delay.

13. The apparatus according to claim 1, wherein said apparatus is configured support a DVD system and provide programmable detect, suppress and anti-noise.

14. The apparatus according to claim 13, wherein said programmable detect is configured on an audio band basis.

15. The apparatus according to claim 1, wherein said noise cancellation circuit is configured to suppress audio with said one or more input signals.

16. The apparatus according to claim 1, wherein said apparatus is configured to support a DVD system with browser VoIP, Internet audio and other browser based audio.

17. The apparatus according to claim 1, wherein said apparatus is configured to perform one or more operations selected from the group consisting of (i) allowing a user to record sound samples, (ii) monitoring for said sound samples and (iii) notifying said user.

18. The apparatus according to claim 1, wherein said apparatus comprises a DVD system and provides multiplexed microphone input with a DVD bitstream, feeds a stationary noise detect function, feeds a stationary noise suppress function, feeds a sound detect function, compares the feed audio to recorded sound samples with an anti-noise function, mixes said audio on an output, and maintains audio/video synchronization.

19. An apparatus comprising:

means for receiving one or more external signals;

means for providing noise reduction on said one or more external signals to generate a processed audio signal, wherein said noise reduction performs (i) noise detection at a first programmable decibel level and (ii) noise suppression at a second programmable decibel level;

means for generating an internal audio signal from a digital source; and means for mixing said internal audio signal and said processed audio signal to generate an output signal.

20. A method for providing noise cancellation of an external source in a DVD system, comprising the steps of:

(A) receiving one or more external signals;

(B) performing (i) noise detection at a first programmable decibel level and (ii) noise suppression at a second programmable decibel level on said external signals to generate a processed audio signal;

(C) generating an internal audio signal from a digital source; and (D) mixing said internal audio signal and said processed audio signal to generate an output signal.

* * * * *